United States Patent

Heine et al.

[11] Patent Number: 5,479,221
[45] Date of Patent: Dec. 26, 1995

[54] HAND-HELD LINE GRID INTERFERENCE RETINOMETER

[75] Inventors: Helmut Heine; Anton Schneider, Geisenbrunn; Otto H. Schmidt, Herrsching, all of Germany

[73] Assignee: Heine Optotechnik GmbH & Co. KG, Herrsching, Germany

[21] Appl. No.: 249,881

[22] Filed: May 26, 1994

[30] Foreign Application Priority Data

May 27, 1993 [DE] Germany .............. 43 17 747.6
Apr. 21, 1994 [DE] Germany .............. 44 13 962.4

[51] Int. Cl.⁶ .................................. A61B 3/10
[52] U.S. Cl. ............... 351/214; 351/211; 351/217; 351/221
[58] Field of Search .................. 351/200, 205, 351/213, 214, 221, 211, 217, 218

[56] References Cited

U.S. PATENT DOCUMENTS

| | | | |
|---|---|---|---|
| 2,352,500 | 6/1944 | Shepard | 351/24 |
| 3,572,910 | 3/1971 | Koester | 351/211 |
| 4,423,931 | 1/1984 | Shapiro | 351/206 |
| 4,447,141 | 5/1984 | Eisenkraft | 251/237 |
| 4,541,697 | 9/1985 | Remijan | 351/211 |
| 4,552,440 | 11/1985 | Guydon | 351/214 |
| 4,801,198 | 1/1989 | Heacock et al. | 351/214 |

FOREIGN PATENT DOCUMENTS 2353122  5/1975  Germany .
2616139 10/1977  Germany .

OTHER PUBLICATIONS

Potential Acuidy Meter Using a Minute Aerial Pinhole Aperture; John S. Mirkowski, Ophthalmology, vol. 90, No. 11, Nov. 1983.
Use of Moiré Fringes for Testing Visual Acuity of the Retina; W. Lotmar; Applied Optics; vol. 11, No. 5; May 1972.
Bernhard Lachenmayr; Potentielle Sehschärfe Bei Störungen Der Brechenden Medien, 1993, 54–94.

Primary Examiner—William L. Sikes
Assistant Examiner—Huy Mai
Attorney, Agent, or Firm—Griffin, Butler, Whisenhunt & Kurtossy

[57] ABSTRACT

An apparatus for testing visual acuity, or clearness of vision, particularly when there is impaired refracting medium in an eye, includes a lamp (1) and a pin-hole diaphragm (4) arranged in a light-beam path downstream of the lamp with a single diffraction grating (6), being provided in the light-beam path downstream of the pin-hole diaphragm.

9 Claims, 3 Drawing Sheets

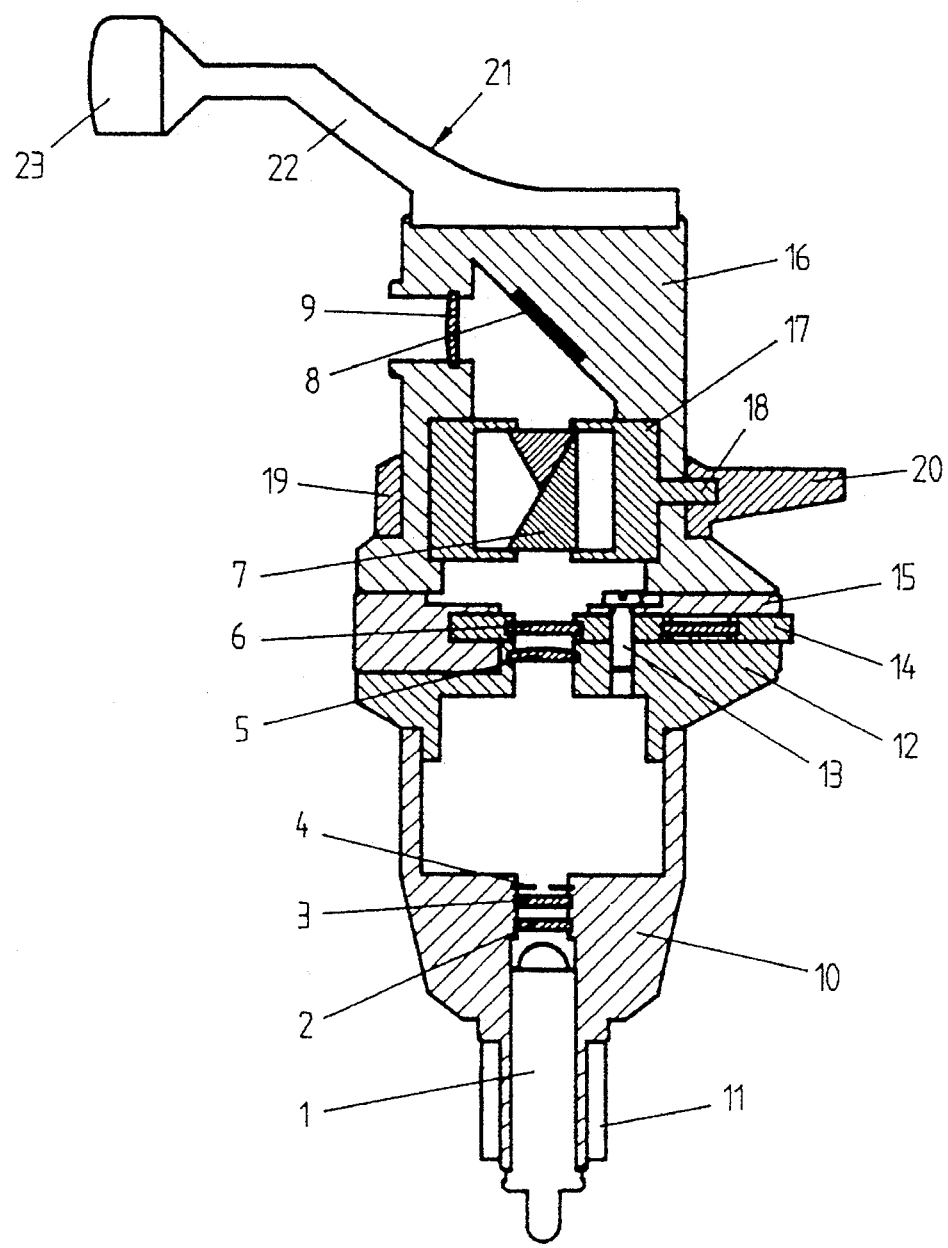
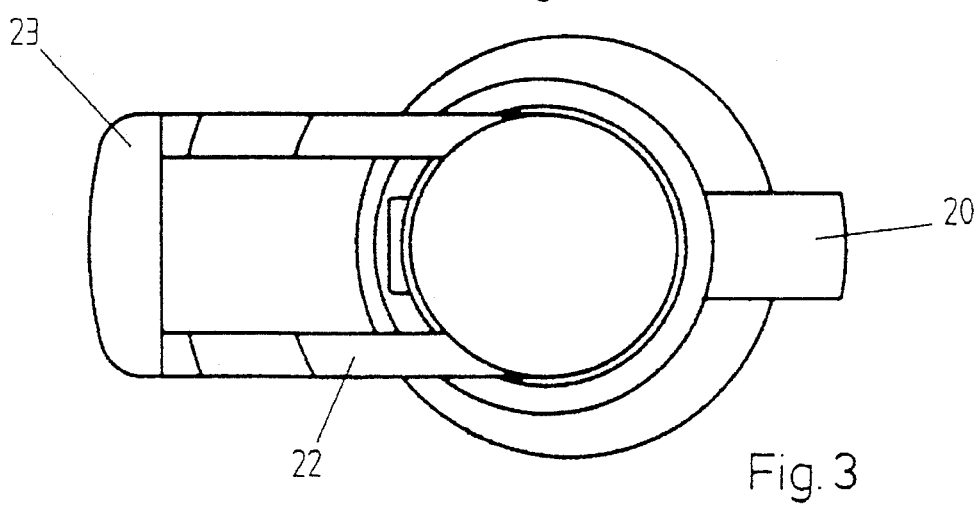
Fig. 3

HAND-HELD LINE GRID INTERFERENCE RETINOMETER

BACKGROUND OF THE BACKGROUND

This invention concerns an apparatus for testing visual acuity or a so called retinometer, which makes possible, particularly when there is impaired refraction medium in an eye, the measuring of potential visual acuity, or clearness of vision.

A book by Bernhard Lachenmayr, "Potential Vision Sharpness With Impaired Refraction Medium" ("Potentielle Sehschärfe bei Störungen der brechenden Medien"), Quintessenz Publishers GmbH (Quintessenz-Verlags-GmbH), Munich, 1993, contains a summarized representation of apparatus known at that time for testing for visual acuity.

A knowledge of retinal visual acuity provides a valuable diagnostic and prognostic aid for an ophthalmologist when a medium is opaque, or clouded. This is particularly the case when it should be decided if an existing vision impairment is caused by opacities of the optical media alone or if vision functions, and information processing therefor, are also disturbed. For example, a cataract operation—replacement of an opaque lens of a patient with an artificial lens—is only practical if reduced visual acuity cannot also be traced to other disease changes.

It is common to previously-known retinometers that a line pattern or a vision test chart is formed on a retina of a patient's eye through a microscopically small area of a refraction medium which is not very opaque, or not opaque at all. This allows a testing substantially independent of impairment of the refraction medium. The smaller the line pattern, or the test characters, that the patient can identify, the better is his vision clearness, and visa versa.

In a retinometer of Rodenstock (see page 83, right column, where indicated) two coherent light beams are produced by reflecting a laser beam on a plano-parallel glass plate which produce, by interference, a line pattern on a retina of a patient. A spacing of the lines is dependent on a thickness of the glass plate. By rotating an intermediate prism the lines can be rotated.

In order to obtain a line pattern with sufficient contrast, high tolerance demands must be made on the glass plate and on the coherence of the laser as well as on guides for the beam path. Unavoidable three dimensional interference patterns (so called speckles) occurring at high line densities interfere with a patient's perception.

Because of optical principles and great optical and mechanical requirements, the device has a large structural length and is quite heavy so that it must usually be stationary. Operation of the laser requires an electrical power connection.

With a SITE-IRAS interferometer (page 88, right column, indicated portions, as well as a prospectus of the firm Interzeag) a microscopically narrow slit illuminated with a light and having a high magnifying objective forms a slit light source imaged just before a holographic grid. This divides the light into two coherent beams of equal intensity. Via a lens system, the two beams are projected into a patient's pupil and create on an eye background, by interference, black and white lines. A line spacing is determined by a position of the movable phase grating along a length of the optical axis, the direction of the lines being changed by simultaneous rotation of the slit and the phase grating.

A contrast of the line patterns depends, on the one hand, on an optical quality of the holographic phase grating, which requires a great expense. On the other hand, use of white light leads to unavoidable spectral refraction, which causes a deterioration of contrast. The axial positioning of the phase grating and parallel rotation of the slit requires great mechanical precision.

This known device can be held in a hand during an examination, however, optical principles require that it have a relatively long structure so that it is uncomfortable to handle. An external power supply is necessary for the lamp which is built into the apparatus, thereby requiring a power hook-up.

A device conceived by Lotmar (page 85, right column, indicated portions) employs two opposingly rotatable, closely-adjacent reticles, or diffraction gratings or line plates. Upon illumination of the recticles with a lamp through a very small slit or a small pin-hole diaphragm, diffraction spectrums arise according to Moiré principles, from which, by means of diaphragms, two adjacent coherent beams of the same order and therefore the same intensity can be separated. By using white light, instead of almost point-like diffraction peaks, spectrally separated diffraction distributions are produced. With a dispersion prism in a beam path the spectral divisions can be united again into white light, so that a black and white line pattern is developed on a retina. By rotation of the two line plates through very small angles, line spacing can be changed while the direction of the line pattern can be moved by the prism.

The optical principles of this device require a great structural length and a very large expense for necessary precision to opposingly rotate the line plates, or discs, through different size angles in fine steps. Application of Moiré-principles requires an extremely high intensity lamp whereby only a commercial power hook-up operation is possible. Thus, this device is also operated from a stationary position.

With the Potential Acuity Meter (PAM) of the firm Mentor (page 72, right column, indicated portions) a smaller chart with test characters of various sizes is projected onto a retina. For correcting refraction errors of an examined eye, the positions of the chart can be moved axially by a rotation knob.

To avoid unclearness caused by diffraction, which particularly disturbs the contrast of small optical characters and thereby makes them difficult to recognize, use of larger test characters, or marks, is required. Because image sharpness of projection systems is distance sensitive, the optical system of PAM must be adjusted for refraction of an examined eye by respectively moving the test characters so as not to get false results from the visual examination. This requires a relatively large mechanical expense, a large structural length, and a high light intensity so that the device must be stationary and coupled to a commercial power source.

A requirement for optically adjusting this device requires an additional expenditure of time and work for difficult patients at a beginning of an examination as well as during it. A correction for astigmatic refraction is not provided for by this device and must be handled by a patient's eyeglasses or other eyeglasses.

Known retinometers are, with the exception of the SITE IRAS device, hindered by their structural size, since they are only suitable to be placed in operation at stationary sites. In order to carry out a visual acuity examination, a patient must come to the device and to the doctor, which, for example, is impossible for those in bed or who are immobile for other reasons. A stationary structure is however also disadvantageous for mobile patients as well because they are required to spend many minutes in bent-over or uncomfortable sitting positions, which makes it difficult, particularly for older persons who form the majority of patients. The only known non-stationary device (SITE IRAS) has a relatively large structural length and requires also a power connection so that it only has limited mobility.

It is an object of this invention to provide an apparatus for testing for visual acuity having a structural length which is small and which does not have undue requirements for precision of optical and mechanical elements.

SUMMARY OF THE INVENTION

According to principles of this invention, an apparatus for testing visual acuity, particularly when there is impaired refraction medium in an eye, comprises a light source and a pin-hole diaphragm arranged in a light-beam path downstream of the light source with a single lined, or reticle, disc being provided in the light-beam path downstream of the pin-hole diaphragm.

BRIEF DESCRIPTION OF THE DRAWING

The invention is described and explained in more detail below using the embodiments shown in the drawings. The described and drawn features, in other embodiments of the invention, can be used individually or in preferred combinations. The foregoing and other objects, features and advantages of the invention will be apparent from the following more particular description of a preferred embodiment of the invention, as illustrated in the accompanying drawings in which reference characters refer to the same parts throughout the different views. The drawings are not necessarily to scale, emphasis instead being placed upon illustrating principles of the invention in a clear manner.

FIG. 2 is a schematic, length-wise, cross sectional view of a preferred embodiment of the apparatus of this invention;

FIG. 3 is a top plan view of the apparatus in FIG. 2; and

DESCRIPTION OF THE PREFERRED EMBODIMENT

Figure 1:
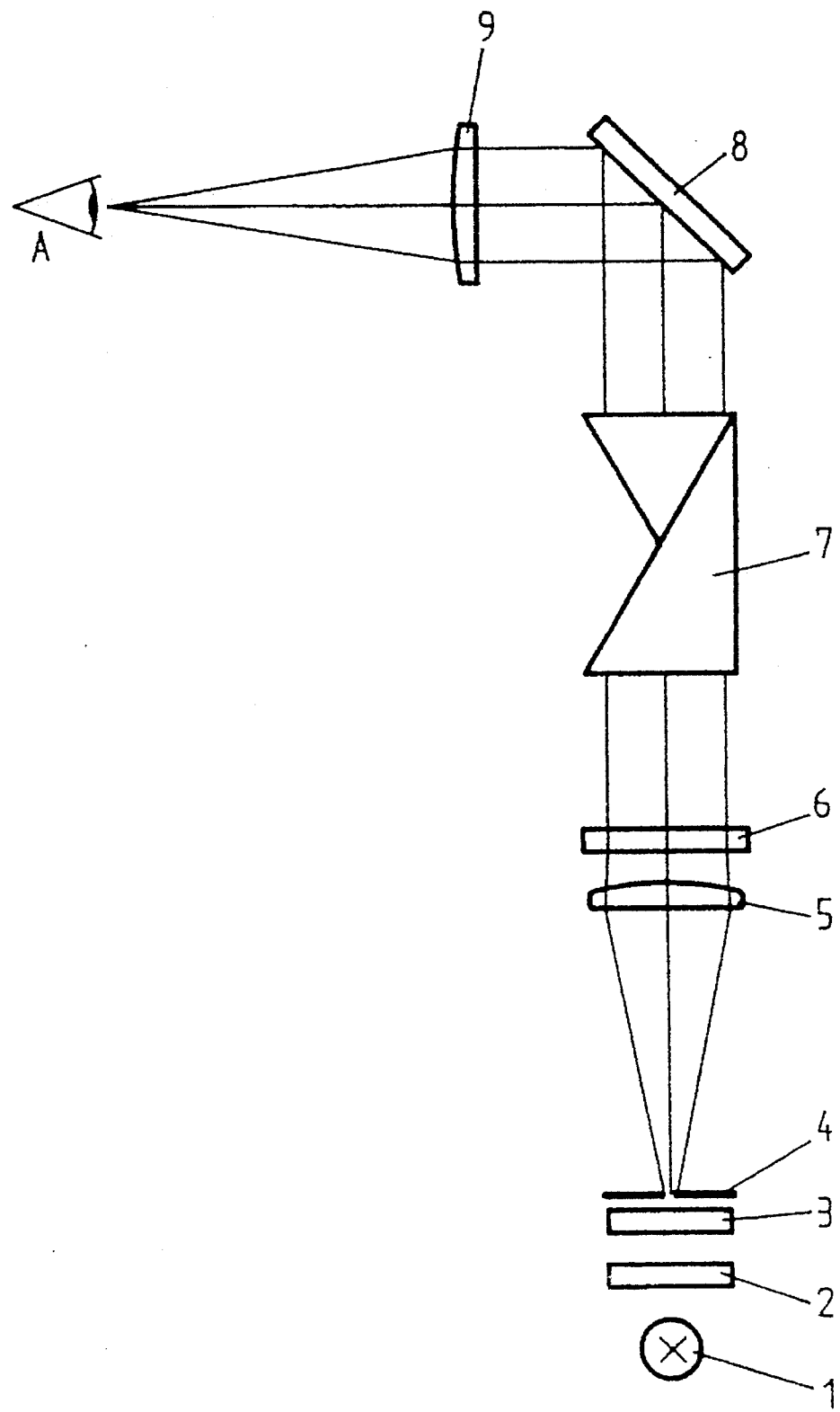
FIG. 1 is a schematic diagram showing a principal light-beam path of an apparatus of this invention for testing visual acuity, with main elements of the apparatus being depicted thereon.
Figure 4:
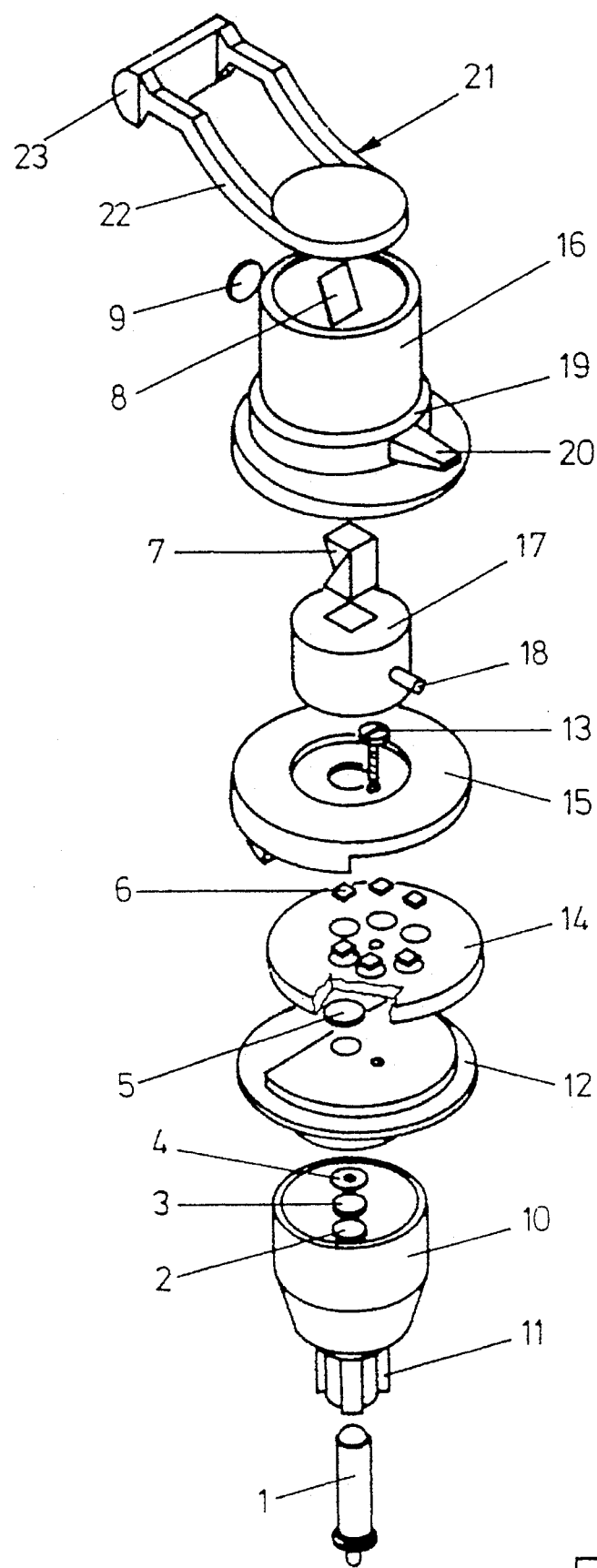
FIG. 4 is an exploded isometric view of the apparatus of FIG. 2.

FIG. 1 shows schematically main structural elements of an apparatus of this invention for testing visual acuity. An incandescent lamp, or light source, 1, shines a beam through a frosted glass, or otherwise translucent screen or diffuser, 2 and a color filter 3. Following the color filter 3, downstream in the light-beam path, are a pin hole diaphragm 4, a first lens 5, a reticle (line grid, line disc or diffraction grating) 6, a prism 7 which is rotatable about its length axis, a deflection mirror 8, and a second lens 9 which projects a diffraction spectrum created by the line disc or diffraction grating in an eye A and onto a retina of a patient.

FIG. 2 shows a schematic length-wise cross section of a practical embodiment of the apparatus of this invention. A lower part 10 of a housing supports at its lower end a foot 11 for plugging the apparatus into a battery handle (not shown). The lamp 1, the frosted glass 2, the color filter 3 and the pin hole diaphragm 4 are received in the foot 11 and in the lower end of the housing 10.

If it is desired to place more color filters 3 of different colors in the light-beam path, these can be placed in a straight-line-slidable slide or on a rotatable plate, as is described below for the line disc(s). Also, it is possible to provide a diffraction grating not on a particular disc, but rather on one or more color filters 3 and to use these combinations instead of the separate line disc(s) 6. A support 12 is mounted on the lower part 10 of the housing which holds the first lens 5 and on which a plate 14, which supports a plurality of line discs with various line widths and/or various line spacings to be placed in the light-beam path, is rotatably mounted. An intermediate ring 15 is placed on the support 12, along with the plate 14. A screw 13 extends through a corresponding hole in the intermediate ring 15 and is screwed into the support 12 so that the plate 14 is thereby rotatably held.

An upper part 16 of the housing is mounted on the intermediate ring 15.

By means of a suitable mechanism the lined discs can be individually rotated to adjust positions of images of line patterns on the retina of the patient. Also, it is possible to provide respectively more lined discs of the same reticle line width and the same reticle spacing, for which only the lines are arranged in respectively different positions.

Preferably, however, a prism holder 17 is provided in the upper part 16 of the housing in the light-beam path downstream, or following, of the plate 14, which, by means of knurled rings on its outer circumference, can be rotated about its rotational axis formed by the screw 13 so that it, together with the prism 7, is rotatable about an axis parallel to the light-beam path. A stud 18 of the holder 17 engages through a groove of the upper part of the housing 16 in an adjusting ring 19 rotatably mounted on the upper part 16 and which has a handle 20.

The deflection mirror 8 and the second lens 9 are arranged in the light-beam path downstream of the prism 7.

A forehead support 21 is on the upper part 16 of the housing which has two arms at whose outer ends a cushion 23 is arranged. The forehead support 21 makes it possible to place the apparatus against a forehead of a patient for holding it at a fixed position from the eye of the patient.

Once the apparatus has been plugged into a battery hand grip and the lamp 1 has been turned on its lamp illuminates, through the translucent screen 2 and the color filter 3, the pin hole diaphragm 4. The light which is directed through the diffraction grating of the reticle plate 6 by the first lens 5 is split by diffraction into rays of various orders. The diffraction spectrum is, after it passes through the prism 7, deflected by the mirror 8 and projected into a pupil of the patient's eye A through the second lens 9. By superimposing at least two of the diffraction rays a pattern of black lines on a colored background, corresponding to the color of the filter 3, is created on the retina by interference. By rotating the plate 14 various lined discs 6 with various line widths and/or various line spacings can be switched into the light-beam path whereby a vision testing is made possible. The reaction of the patient to rotation to the line pattern on his retina by rotating the prism 7 is used in the examination.

To carry out a vision test an examiner places the forehead support 21 of the apparatus on a patient's forehead and directs the fine light rays coming out of the second lens 9 on a pupil of the patient. During this the examiner views beside the apparatus or over the apparatus through an opening between both arms 22 the eye of the patient and observes the points of light. The patient can, thereby, be in any desired position.

The invention is based on a principle that employment of a single lined disc is sufficient to create a line pattern having sufficient contrast on a retina, whereby most or all of the deficiencies of known apparatus can be avoided. The lined disc can be easily and inexpensively manufactured. Even when one employs more lined discs with various line widths and various line spacings which are arranged on a support and switched into the light-beam path individually, the expense for manufacturing the entire apparatus remains quite small. The apparatus can be operated independently of power mains and has a very small structural size. It is therefore comfortable to manipulate.

The lined disc can be mounted for rotation, at a very small expense, for adjusting the line patterns projected on a retina of a patient. If a plurality of lined discs with various line widths/spacings were arranged on a support, however, the construction costs for then providing rotation of the lined discs would be relatively great. Therefore it is preferable to arrange a prism, which is rotatable about an axis parallel to the light path, in the light-beam path downstream of the lined disc.

Preferably, a color filter is provided in the light-beam path between the lamp and the following pin-hole in order to increase the contrast of the line pattern and to give the line pattern a particular color of light especially suitable for examinations. In a further embodiment a translucent, or frosted surface is provided in the light-beam path between the lamp and the downstream pin-hole with which an image of a filament of an incandescent lamp is diffused so that an increase in contrast of the line pattern is achieved. The frosted lens, or surface, can, for example, be directly on a light bulb or in the form of a one or two frosted-sided glass screen or also as a frosted surface on one or both sides of the filter.

A further beneficial embodiment results if a lens lamp is employed which makes better use of light and thereby makes possible a reduced lamp capacity.

In order to hold the apparatus at a fixed distance from a patient's eye, the forehead support is preferably attached to the housing. The forehead support is preferably of two parallel arms which are spaced from one another so that an empty space is formed between them for allowing a field of vision to the patient's eyes.

The embodiments of the invention in which an exclusive property or privilege are claimed are defined as follows:

1. Apparatus for testing visual acuity of an eye of a patient, particularly when there is impaired refracting medium in the eye, comprising a light source (1) and a pin-hole diaphragm (4) arranged in a light-beam path downstream of the light source, wherein only a single diffraction line grid (6) is provided in the light-beam path following the pin-hole diaphragm (4) for creating a line pattern on a retina of the eye of the patient by causing a diffraction spectrum and creating an interference line pattern on the retina.

2. Apparatus as in claim 1 wherein is further included a plate (14) having a plurality of line discs each with only a single line grid arranged thereon about a concentric circular arc so that they can be individually, only one at a time, moved into the light-beam path.

3. Apparatus as in claim 1 wherein is further included a prism arranged in the light-beam path following the pin-hole diaphragm, which prism is rotatable about an axis parallel to the light-beam path.

4. Apparatus as in claim 1 wherein is further included a color filter which is arranged in the light-beam path between the light source and the following pin-hole diaphragm.

5. Apparatus as in claim 1 wherein at least one light diffuser is arranged in the light-beam path between the light source and the following pin hole diaphragm.

6. Apparatus as in claim 1 wherein the light source is a lamp having a frosted bulb surface.

7. Apparatus as in claim 1 wherein the light source is formed as a lens lamp having an optical lens thereon.

8. Apparatus as in claim 1 wherein a forehead support is attached to a housing for said apparatus for testing visual acuity.

9. Apparatus as in claim 8 wherein the forehead support comprises two parallel, spaced-from-one-another, arms so that there is an opening between the arms to allow a field of vision to the patient's eyes.

* * * * *